United States Patent
Sander et al.

(10) Patent No.: US 6,740,130 B2
(45) Date of Patent: May 25, 2004

(54) HAIR-COLORANT PREPARATIONS AND METHODS OF USING THE SAME

(75) Inventors: Celia Sander, Duisburg (DE); Anke Eggers, Duesseldorf (DE); Josef Koester, Duesseldorf (DE); Werner Seipel, Hilden (DE); Hermann Hensen, Haan (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 41 days.

(21) Appl. No.: 10/235,601

(22) Filed: Sep. 5, 2002

(65) Prior Publication Data

US 2003/0061668 A1 Apr. 3, 2003

Related U.S. Application Data

(63) Continuation of application No. 10/018,276, filed as application No. PCT/EP00/05172 on Jun. 6, 2000, now abandoned.

(30) Foreign Application Priority Data

Jun. 6, 1999 (DE) .......................... 199 27 076

(51) Int. Cl.$^7$ ................................. A11K 7/13
(52) U.S. Cl. ................ 8/405; 8/406; 8/512; 8/582
(58) Field of Search ................ 8/405, 406, 512, 8/582

(56) References Cited

U.S. PATENT DOCUMENTS

| | | | |
|---|---|---|---|
| 4,172,887 A | 10/1979 | Vanlerberghe et al. | 424/70 |
| 4,283,384 A | 8/1981 | Jacquet et al. | 424/47 |
| 5,876,705 A | 3/1999 | Uchiyama et al. | 424/70.12 |

FOREIGN PATENT DOCUMENTS

| | | |
|---|---|---|
| DE | 1 165 574 A | 3/1964 |
| DE | 20 24 051 C3 | 10/1979 |
| DE | 39 14 131 A1 | 10/1990 |
| DE | 44 11 557 A1 | 10/1995 |
| EP | 0 697 206 A1 | 2/1996 |
| FR | 2 252 840 | 8/1975 |
| GB | 962919 A | 7/1964 |
| GB | 1 333 475 | 10/1973 |
| GB | 2 242 358 A | 10/1991 |
| WO | WO 98/27944 | 7/1998 |

OTHER PUBLICATIONS

Falbe, "Surfactants in Consumer Products", Springer Verlag, Berlin, (1987), pp. 54–124.
Falbe, "Katalysatoren, Tenside und Mineraloladditive", Thieme Verlag, Stuttgart, (1987), pp. 123–213.
"Kosmetische Färbemitte!", Farbstoffkommission der Deutschen Forschungsgemeinschaft, Verlag Chemie, Weinheim, (1984), pp. 81–106.
Eiche, "Mikroemulsionen–eine wissenschaftliche und anwendungstechnische Fundgrube?", SÖFW–Journal, vol. 118, (May, 1992), pp. 311–315.
Förster, et al., "Neuartige Körperpflegemittel auf Basis von Mikroemulsionen mit Alkylpolyglykosiden", SÖFW–Journal, vol. 122, (Nov., 1996), pp. 746, 748, 750 & 753.
Todd, et al., "Volatile silicone fluids for cosmetic formulations", Cosmetics and Toiletries, vol. 91, (Jan. 5, 1976), pp. 29–32.
Wortmann, et al., "Characterizing Keratins Using High–Pressure Differential Scanning Calorimetry(HPDSC)", Journal of Applied Polymer Science, vol. 48, John Wiley & Sons, Inc., (1993), pp. 137–150.

Primary Examiner—Yogendra N. Gupta
Assistant Examiner—Eisa Elhilo
(74) Attorney, Agent, or Firm—John E. Drach; Aaron R. Ettelman

(57) ABSTRACT

Hair-colorant compositions containing (a) from 0.2 to 25% by weight of an alkoxylated carboxylic acid ester; (b) from 0.5 to 25% by weight of a fatty acid partial glyceride; and (c) from 0.1 to 15% by weight of a hair dye; wherein all percentages by weight are based on the total composition, are disclosed. Methods of reducing cloudiness in hair-colorant compositions by combining a hair dye and a mixture of an alkoxylated carboxylic acid ester and a fatty acid partial glyceride are also disclosed.

20 Claims, No Drawings

HAIR-COLORANT PREPARATIONS AND METHODS OF USING THE SAME

CROSS-REFERENCE TO RELATED APPLICATIONS

This application claims priority under 35 U.S.C. §120, and is a continuation of, U.S. patent application Ser. No. 10/018,276, filed on Dec. 12, 2001 as a 35 U.S.C. §371 submission based upon International Application No. PCT/EP00/05172, having an International Filing Date of Jun. 6, 2000, the entire contents of which are herein incorporated by reference.

BACKGROUND OF THE INVENTION

Preparations used to color and care for the hair generally contain one or more surfactants, more particularly based on anionic or amphoteric surfactants. However, the sole use of surfactants in hair coloring preparations, for example creams of the oil-in-water type, would result in the hair drying out so that hair-care additives are generally incorporated. There is still a need to provide hair coloring preparations which would afford the hair even greater protection during coloring and which would also counteract damage to the hair structure by coloring processes and would be dermatologically compatible. These preparations would be further distinguished by high stability, even when stored at elevated temperatures.

Accordingly, the problem addressed by the invention was to provide hair coloring preparations which, after use, would cause little damage to the hair and would stabilize it and which would therefore keep the hair structure intact. These mixtures would also be dermatologically safe and would be distinguished by high stability in storage at elevated temperatures.

BRIEF SUMMARY OF THE INVENTION

The present invention relates, in general, to hair-colorant preparations containing mixtures of alkoxylated carboxylic acid esters, fatty acid partial glycerides and hair dyes, and to the use of such mixtures as wetting agents in the production of hair coloring preparations.

The present invention relates to hair coloring preparations containing (a) 0.2 to 25% by weight of alkoxylated carboxylic acid esters,
(b) 0.5 to 25% by weight of fatty acid partial glycerides and
(c) 0.1 to 15% by weight of hair dyes, with the proviso that the quantities shown add up to 100% by weight with water and optionally other auxiliaries and additives.

It has surprisingly been found that hair coloring preparations, preferably o/w cream preparations, which contain a mixture of alkoxylated carboxylic acid esters, selected partial glycerides and coloring preparations lead to an improvement in hair structure and hence to stabilization and preservation of the hair. The invention includes the observation that the mixtures in question also protect the hair against drying out and moisture loss and thus contribute towards preservation of the hair. The mixtures also have a refatting effect and are dermatologically very safe. The resulting hair preparations are distinguished by particularly high stability, even when stored at elevated temperatures.

DETAILED DESCRIPTION OF THE INVENTION

Alkoxylated Carboxylic Acid Esters

The alkoxylated carboxylic acid esters which the preparations according to the invention must contain as component (a) are known from the prior art. They may be obtained, for example, by esterification of alkoxylated carboxylic acids with alcohols. For the purposes of the present invention, however, the compounds are preferably produced by reaction of carboxylic acid esters with alkylene oxides using catalysts, more especially calcined hydrotalcite in accordance with DE-A-3914131 A, which give compounds with a narrow homolog distribution. Carboxylic acid esters of both monohydric alcohols and dihydric alcohols can be alkoxylated by this process. Alkoxylated carboxylic acid esters of monohydric alcohols corresponding to general formula (I):

$$R^1CO(OAlk)_nOR^2 \quad\quad (I)$$

in which $R^1CO$ is an aliphatic acyl group derived from a carboxylic acid, AlkO stands for alkylene oxide and $R^2$ is an aliphatic alkyl group derived from a monohydric aliphatic alcohol, are preferred for the purposes of the invention. Alkoxylated carboxylic acid esters of formula (I), in which $R^1CO$ is an aliphatic acyl group containing 6 to 30, preferably 6 to 22 and more particularly 10 to 18 carbon atoms, AlkO stands for a $CH_2CH_2O—$, $CHCH_3CH_2O—$ and/or $CH_2—CHCH_3O$ group, n has an average value of 1 to 30, preferably 5 to 20 and more particularly 10 to 15 and $R^2$ is a linear or branched alkyl group containing 1 to 4 and preferably 1 and/or 2 carbon atoms, more particularly methyl, are particularly suitable.

Preferred acyl groups are derived from carboxylic acids containing 6 to 22 carbon atoms of natural or synthetic origin, more especially from linear, saturated and/or unsaturated fatty acids, including the technical mixtures thereof obtainable by lipolysis from animal and/or vegetable fats and oils, for example from coconut oil, palm kernel oil, palm oil, soya oil, sunflower oil, rapeseed oil, cottonseed oil, fish oil, bovine tallow and lard. Examples of such carboxylic acids are caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and/or erucic acid.

AlkO stands for the alkylene oxides which are reacted with the carboxylic acid esters and which comprise ethylene oxide, propylene oxide and/or butylene oxides, preferably ethylene oxide and/or propylene oxide and more particularly ethylene oxide on its own.

Alkoxylated carboxylic acid esters corresponding to formula (I), in which $R^1CO$ is a linear or branched, saturated or unsaturated acyl group containing 10 to 18 carbon atoms, AlkO is a $CH_2CH_2O$ group, n is a number of 5 to 20 and $R^2$ is a methyl group, are particularly suitable. Examples of such compounds are lauric acid methyl ester, coconut fatty acid methyl ester and tallow fatty acid methyl ester alkoxylated with on average 5,7,9 or 11 moles ethylene oxide.

The alkoxylated carboxylic acid esters may be used in quantities of 0.2 to 25, preferably 0.2 to 10 and more preferably 1 to 5% by weight, based on the keratin-reducing substance or the oxidizing agent, in the process according to the invention.

Fatty Acid Partial Glycerides

Fatty acid partial glycerides which form component (b), i.e. monoglycerides, diglycerides and technical mixtures thereof, may still contain small quantities of triglycerides from their production. The partial glycerides preferably correspond to formula (II):

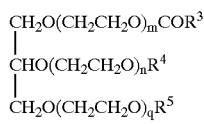
(II)

in which $R^3CO$ is a linear or branched, saturated and/or unsaturated acyl group containing 6 to 22 and preferably 12 to 18 carbon atoms, $R^4$ and $R^5$ independently of one another have the same meaning as $R^3CO$ or represent OH and the sum (m+n+q) is 0 or a number of 1 to 100 and preferably 5 to 25, with the proviso that at least one of the two substituents $R^4$ and $R^5$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Oleic acid monoglycerides are preferably used.

Hair Dyes

Suitable hair dyes which form component (c) are, for example, substantive dyes, for example from the group of nitrophenylenediamines, nitroaminophenols, anthraquinones and indophenols, such as for example the compounds known under the International names or trade names of HC Yellow 2, HC Yellow 4, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16, Basic Brown 17, pricramic acid and Rodol 9 R and also 4-amino-2-nitrodiphenylamine-2'-carboxylic acid, 6-nitro-1,2,3,4-tetrahydroquin-oxaline, (N-2,3-dihydroxypropyl-2-nitro-4-trifluoromethyl)-aminobenzene and 4-N-ethyl-1,4-bis-(2'-hydroxyethylamino)-2-nitrobenzene hydrochloride. Naturally occurring dyes such as, for example, henna red, henna neutral, henna black, camomile blossom, sandalwood, black tea, black alder bark, sage, logwood, madder root, catechu, sedre and alkanet may also be added to the emulsions.

Besides substantive dyes, oxidation dyes consisting of primary and secondary intermediates may also be added to the emulsions. The primary intermediates used are, for example, primary aromatic amines containing another free or substituted hydroxy or amino group in the para or ortho position, diaminopyridine derivatives, heterocyclic hydrazones, 4-amino-pyrazolone derivatives and 2,4,5,6-tetraaminopyrimidine and derivatives thereof. Special representatives are inter alia p-toluylenediamine, p-aminophenol, N,N-bis-(2-hydroxyethyl)-p-phenylenediamine, 2-(2,5-diamino-phenoxy)-ethanol, 1-phenyl-3-carboxyamido-4-amino-5-pyrazolone and 4-amino-3-methylphenol, 2-(2-hydroxyethyl)-1,4-aminobenzene and 2,4,5,6-tetraaminpyrimidine. The secondary intermediates used are generally m-phenylenediamine derivatives, naphthols, resorcinol and resorcinol derivatives, pyrazolones, m-aminophenols and pyridine derivatives. Particularly suitable secondary intermediates are 1-naphthol, pyrogallol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diamino-phenoxy)-propane, 4-chlororesorcinol, 2-chloro-6-methyl-3-aminophenol, 2-methyl resorcinol, 2,5-dimethyl resorcinol, 2,6-dihydroxypyridine and 2,6-diaminopyridine.

So far as other dye components are concerned, reference is specifically made to the Colipa-Liste published by the Industrieverband Körperflege und Waschmittel, Frankfurt. In addition, an overview of suitable dyes can be found in the publication "Kosmetische Färbemittel" of the Farbstoffkommission der Deutschen Forschungs-gemeinschaft, Verlag Chemie, Weinheim, 1984, pages 81 to 106.

Surfactants

The preparations according to the invention may contain anionic and/or amphoteric or zwitterionic surfactants as preferred auxiliaries and additives. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineral öladditive (Catalysts, Surfactants and Mineral Oil Additives)", Thieme Verlag, Stuttgart, 1978, pages 123–217. The surfactants may make up from 0.1 to 10% by weight and preferably from 0.5 to 5% by weight of the preparations.

Oil Components

The preparations according to the invention may contain from 0.5 to 25% by weight and preferably from 1 to 15% by weight of oil components as preferred auxiliaries and additives. Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $Cr1_3$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons. Other suitable oil components are hydrocarbons, such as squalane and squalene.

Polymeric Thickeners

In another preferred embodiment of the invention, the hair coloring preparations also contain polymeric thickeners, such as Aerosil types (hydrophilic silicas), polysaccharides, more especially xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride, as auxiliaries and additives. The polymers may be used in quantities of 0.1 to 5% by weight and preferably 0.5 to 2% by weight, based on the hair coloring preparations.

Fatty Alcohols

The preparations according to the invention may also contain fatty alcohols corresponding to formula (III):

$$R^6 OH \quad (III)$$

in which $R^6$ is an aliphatic, linear or branched, hydrocarbon chain containing 6 to 22 carbon atoms and 0 and/or 1, 2 or 3 double bonds, as preferred auxiliaries and additives. Typical examples are caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, for example coconut, palm, palm kernel or tallow alcohol, are preferred. The percentage content of fatty alcohols in the dispersions may be from 5 to 50% by weight and is preferably from 25 to 40% by weight.

The preparations according to the invention may be produced as fatty alcohol dispersions by the microdispersion process. Microdispersions are optically isotropic, thermodynamically stable systems which contain a water-insoluble component (in the present case fatty alcohol partial glycerides), dispersants (preferably alkyl glucosides) and water. The clear or transparent appearance of the microdispersions is attributable to the small paticle size of the dispersed emulsion droplets. In this connection, it has been found that fatty alcohol microdispersions have a particularly favorable effect on the production and shelf life of the resulting coloring preparations. Preferred dispersions have a particle size below 50 μm, more particularly below 20 μm and most preferably below 10 μm. Overviews of the production and use of microdispersions have been published by H. Eicke in SÖFW-Journal, 118, 311 (1992) and by Th. F örster et al. in SÖFW-Journal, 122, 746 (1996); reference is also made to DE-A1 4411557 (Henkel) and EP 0687206 A1 (L'Oréal).

Commercial Applications

The present invention also relates to preparations containing (a) 0.2 to 25, preferably 5 to 20 and more preferably 10 to 15% by weight of alkoxylated carboxylic acid esters, (b) 0.5 to 25, preferably 5 to 20 and more preferably 10 to 15% by weight of fatty acid partial glycerides and (c) 0.1 to 15, preferably 0.5 to 10 and more preferably 1 to 5% by weight of hair dyes, with the proviso that the quantities shown add up to 100% by weight with water and optionally other auxiliaries and additives, as consistency factors for the production of hair coloring preparations, preferably o/w coloring creams.

Auxiliaries and Additives

The hair coloring preparations according to the invention are preferably o/w creams which may contain co-emulsifiers, superfatting agents, pearlizing waxes, consistency factors, polymers, silicone compounds, fats, waxes, stabilizers, film formers, swelling agents, hydrotropes, preservatives, solubilizers, complexing agents, reducing agents, alkalizing agents, antioxidants, perfume oils and the like as additional auxiliaries and additives.

The surfactants present in the preparations may also serve as emulsifiers in the final preparations. In addition, other surfactants or co-emulsifiers may also be added to the hair coloring preparations, including for example (1) Products of the addition of 2 to 30 moles ethylene oxide and/or 0 to 5 moles propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of addition products of 1 to 30 moles of ethylene oxide with glycerol;

(3) glycerol mono- and diesters, sorbitan mono- and diesters of saturated and unsaturated fatty acids containing 6 to 22 carbon atoms and ethylene oxide addition products thereof;

(4) alkyl mono- and oligoglycosides containing 8 to 22 carbon atoms in the alkyl group and ethoxylated analogs thereof;

(5) addition products of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate isostearate. Mixtures of compounds from several of these classes are also suitable;

(7) addition products of 2 to 15 moles of ethylene oxide with castor oil and/or hydrogenated castor oil;
(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(9) mono-, di and trialkyl phosphates and mono-, di- and/or tri-PEG-alkyl phosphates and salts thereof;
(10) wool wax alcohols;
(11) polysiloxane/polyalkyl polyether copolymers and corresponding derivatives;
(12) mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol,
(13) polyalkylene glycols and
(14) glycerol carbonate.

The addition products of ethylene oxide and/or propylene oxide with fatty alcohols, fatty acids, alkyl phenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE 2024051 PS.

$C_{8/18}$ alkyl mono- and oligoglycosides, their production and their use are known from the prior art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Other suitable emulsifiers besides ampholytic surfactants are quaternary emulsifiers, those of the esterquat type, preferably methyl-quaternized difatty acid triethanolamine ester salts, being particularly preferred Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlescing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®), Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/ acrylate copolymers, octylacrylamide/methyl methacrylate/ tert.-butylaminoethyl methacrylate/2-hydroxypropyl methacrylate copolymers, polyvinyl pyrrolidone, vinyl pyrrolidone/vinyl acetate copolymers, vinyl pyrrolidone/ dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to $\mu$mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Suitable complexing agents are EDTA, NTA, phosphonic acids, Triton B, turpinal and phenazetin. In addition, reducing agents such as, for example, ascorbic acid, sodium sulfate, sodium thiosulfate and the like may also be present. Suitable alkalizing agents are ammonia, monoethanolamines, (L)-arginine, AMP, etc.

Suitable perfume oils are mixtures of natural and synthetic perfumes. Natural perfumes include the extracts of blossoms (lily, lavender, rose, jasmine, neroli, ylang—ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

The total percentage content of auxiliaries and additives may be from 1 to 50% by weight and is preferably from 5 to 40% by weight, based on the particular preparation. The preparations may be produced in known manner, i.e. for example by hot, cold, hot—hot/cold or PIT emulsification. This is a purely mechanical process which does not involve a chemical reaction.

EXAMPLES

Hair coloring preparations containing mixtures 1 and 2 according to the invention and comparison mixture C1 were prepared. After application of these hair coloring creams, a thermal analysis of human hair (Alkinco 6634) was carried out to investigate the structure. Using dynamic differential calorimetry (HP-DSC; F. J. Wortmann et al., J. Appl. Polym. Sci. 1993, 48, pp. 137 et seq), the transition point of the treated hair sample can be measured by comparison with an untreated hair sample (H–DSC=152.5° C.). Stability was visually determined after storage for 4 weeks at 40° C. by observing clouding behavior (+=cloudy; −=non-cloudy).

The results are set out in Table 1.

TABLE 1

Effect of o/w hair coloring creams on the hair and stability of the creams (quantities = % by weight active substance)

| Composition/Performance | 1 | 2 | C1 |
|---|---|---|---|
| $C_{12/18}$ Coconut fatty acid + 2EO methyl ester | 6 | 4 | — |
| Monomuls ® 90-O18 Glyceryl Oleate | 10 | 10 | — |
| HC Yellow | 1.0 | 1.5 | 1.0 |
| Lanette ® O Cetysteryl Alcohol | 5 | — | 5 |
| Ammonia | 2.0 | 2.0 | 2.0 |
| Ammonium chloride | 0.5 | 0.5 | 0.5 |
| Tetrasodium EDTA | 0.5 | 0.5 | 0.5 |
| Dehyquart ® E-CA Hydroxycetyl Hydroxyethyl Dimonium Chloride | 1.0 | 1.0 | 1.0 |
| Texapon ® N70 | 2.5 | 2.5 | 2.5 |
| Sodium sulfite | 1.0 | 1.0 | 1.0 |
| N,N'-bis-(4-aminophenyl)-piperidine | 5.0 | 5.0 | 5.0 |
| Resorcinol | 5.0 | 5.0 | 5.0 |
| Water | | to 100 | |
| Stability after 4 w (40° C.) | − | − | + |
| Transition point (HP-DSC) | 150.7 | 151.1 | 149.8 |

What is claimed is:

1. A hair-colorant composition comprising:
   (a) from 0.2 to 25% by weight of an alkoxylated carboxylic acid ester;
   (b) from 0.5 to 25% by weight of a fatty acid partial glyceride; and
   (c) from 0.1 to 15% by weight of a hair dye;
wherein all percentages by weight are based on the composition.

2. The hair-colorant composition according to claim 1, wherein the alkoxylated carboxylic acid ester corresponds to the general formula (I):

$$R^1CO(OAlk)_nOR^2 \qquad (I)$$

wherein $R^1CO$ represents an aliphatic acyl group having from 6 to 30 carbon atoms, each AlkO independently represents an alkoxylate selected from the group consisting of $CH_2CH_2O-$, $CH(CH_3)CH_2O-$ and $CH_2CH(CH_3)O-$, n represents a number of from 1 to 30, and $R^2$ represents an aliphatic alkyl group having from 1 to 4 carbon atoms.

3. The hair-colorant composition according to claim 2, wherein $R^1CO$ represents an aliphatic acyl group having from 10 to 18 carbon atoms, each AlkO represents an ethoxylate group, n represents a number of from 5 to 20, and $R^2$ represents a methyl group.

4. The hair-colorant composition according to claim 1, wherein the alkoxylated carboxylic acid ester comprises an ethoxylated methyl ester of an acid selected from the group consisting of lauric acid, coconut fatty acid, and tallow fatty acid, wherein the alkoxylated carboxylic acid ester has an average degree of ethoxylation of from 5 to 11.

5. The hair-colorant composition according to claim 1, wherein the alkoxylated carboxylic acid ester is present in an amount of from 5 to 20% by weight based on the composition.

6. The hair-colorant composition according to claim 3, wherein the alkoxylated carboxylic acid ester is present in an amount of from 5 to 20% by weight based on the composition.

7. The hair-colorant composition according to claim 1, wherein the alkoxylated carboxylic acid ester is present in an amount of from 10 to 15% by weight based on the composition.

8. The hair-colorant composition according to claim 1, wherein the fatty acid partial glyceride corresponds to the general formula (II):

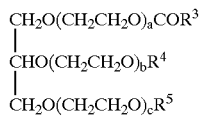
(II)

wherein $R^3CO$ represents an acyl group having from 6 to 22 carbon atoms, $R^4$ and $R^5$ each independently of one another have the same meaning as $R^3CO$ or represent OH and the sum (a+b+c) is a number of from 0 to 100, with the proviso that at least one of $R^4$ and $R^5$ represents OH.

9. The hair-colorant composition according to claim 1, wherein the fatty acid partial glyceride is present in an amount of from 5 to 20% by weight based on the composition.

10. The hair-colorant composition according to claim 8, wherein the fatty acid partial glyceride is present in an amount of from 5 to 20% by weight based on the composition.

11. The hair-colorant composition according to claim 1, wherein the fatty acid partial glyceride is present in an amount of from 10 to 15% by weight based on the composition.

12. The hair-colorant composition according to claim 1, wherein the hair dyes is selected from the group consisting of substantive dyes and oxidative dyes.

13. The hair-colorant composition according to claim 1, wherein the hair dye is present in an amount of from 0.5 to 10% by weight based on the composition.

14. The hair-colorant composition according to claim 12, wherein the hair dye is present in an amount of from 0.5 to 10% by weight based on the composition.

15. The hair-colorant composition according to claim 1, wherein the hair dye is present in an amount of from 1 to 5% by weight based on the composition.

16. The hair-colorant composition according to claim 1, further comprising a surfactant.

17. The hair-colorant composition according to claim 1, further comprising an oil component.

18. The hair-colorant composition according to claim 1, wherein the alkoxylated carboxylic acid ester is present in an amount of from 5 to 20% by weight, wherein the fatty acid partial glyceride is present in an amount of from 5 to 20% by weight, and wherein the hair dye is present in an amount of from 0.5 to 10% by weight; wherein all percentages by weight are based on the composition.

19. A hair-colorant composition comprising:

(a) from 10 to 15% by weight of an alkoxylated carboxylic acid ester, wherein the alkoxylated carboxylic acid ester comprises an ethoxylated methyl ester of an acid selected from the group consisting of lauric acid, coconut fatty acid, and tallow fatty acid, wherein the alkoxylated carboxylic acid ester has an average degree of ethoxylation of from 5 to 11;

(b) from 10 to 15% by weight of a fatty acid partial glyceride, wherein the fatty acid partial glyceride corresponds to the general formula (II):

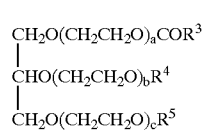
(II)

wherein $R^3CO$ represents an acyl group having from 6 to 22 carbon atoms, $R^4$ and $R^5$ each independently of one another have the same meaning as $R^3CO$ or represent OH and the sum (a+b+c) is a number of from 0 to 100, with the proviso that at least one of $R^4$ and $R^5$ represents OH; and (c) from 1 to 5% by weight of a hair dye;

wherein all percentages by weight are based on the composition.

20. A method of reducing cloudiness in hair-colorant compositions, said method comprising:

(a) providing a hair-colorant composition comprising a hair dye;

(b) providing a mixture of (i) an alkoxylated carboxylic acid ester and (ii) a fatty acid partial glyceride; and (c) combining the hair-colorant composition and the mixture.

* * * * *